United States Patent [19]

Bentley et al.

[11] 4,394,375
[45] Jul. 19, 1983

[54] CEPHALOSPORIN DERIVATIVES, AND COMPOSITIONS CONTAINING THEM

[75] Inventors: Peter H. Bentley; Kenneth D. Hardy; Peter H. Milner, all of Horsham, England

[73] Assignee: Beecham Group Limited, England

[21] Appl. No.: 271,008

[22] Filed: Jun. 5, 1981

[30] Foreign Application Priority Data

Jun. 6, 1980 [GB] United Kingdom ............... 8018674

[51] Int. Cl.$^3$ .................. A61K 31/545; C07D 501/57
[52] U.S. Cl. .................................. 424/114; 424/270; 424/246; 424/248.4; 544/21; 544/28; 544/90
[58] Field of Search ................... 544/21, 90, 26, 27, 544/30; 424/246, 114, 114, 248.4

[56] References Cited

U.S. PATENT DOCUMENTS

| | | | |
|---|---|---|---|
| 4,108,992 | 8/1978 | Pearson et al. | 544/90 |
| 4,167,630 | 9/1979 | Finestine | 544/90 |
| 4,200,744 | 4/1980 | Saikawa et al. | 544/21 |
| 4,272,439 | 6/1981 | Ganguly et al. | 544/21 |
| 4,293,555 | 10/1981 | Christensen et al. | 260/245.3 |
| 4,321,265 | 3/1982 | Saikawa et al. | 544/21 |

FOREIGN PATENT DOCUMENTS 1366682  9/1974  United Kingdom .

Primary Examiner—Nicholas S. Rizzo
Attorney, Agent, or Firm—Jacobs & Jacobs

[57] ABSTRACT

A compound of formula (I) or a pharmaceutically acceptable salt or in vivo hydrolysable ester thereof:

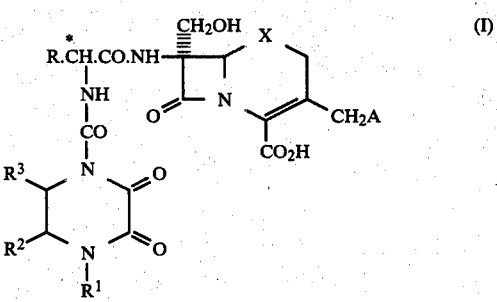

wherein
R is phenyl, 4-hydroxyphenyl, or a 5- or 6-membered heterocyclic ring containing up to three heteroatoms selected from oxygen, sulphur or nitrogen, optionally substituted with hydroxy, amino, halogen or $C_{1-6}$ alkoxy;
$R^1$ represents hydrogen or $C_{1-6}$ alkyl;
$R^2$ and $R^3$ are the same or different and represent hydrogen, $C_{1-6}$ alkyl, halogen, amino, hydroxy, or $C_{1-6}$ alkoxy;
X represents oxygen or sulphur; and
A represents hydrogen, pyridyl, acetoxy, carbamoyloxy or a heterocyclicthio group;

Their preparation and use is described.

13 Claims, No Drawings

CEPHALOSPORIN DERIVATIVES, AND COMPOSITIONS CONTAINING THEM

This invention relates to a class of cephalosporin derivatives which have antibacterial activity and are of value in the treatment of infections in animals, including man and poultry, caused by a wide range of organisms, particularly Gram-negative organisms. In particular the invention relates to a class of 7α-hydroxymethyl cephalosporin derivatives. The invention also relates to a process for the preparation of such compounds, and to pharmaceutical compositions comprising them.

British Patent specification No. 1,366,682 discloses inter alia a class of 7-substituted acylamino cephalosporin of general formula (A):

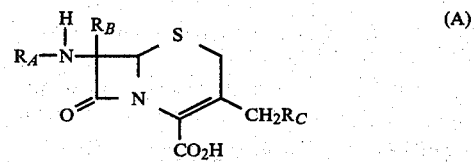

in which $R_A$ is an acyl radical; $R_C$ is hydrogen, halogen, hydroxy, mercapto, cyano, $C_{1-6}$ alkanoyloxy, $C_{1-6}$ alkanoylthio, aroyloxy, aroylthio, heteroaryloxy or heteroarylthio in which the hetero ring has 5-6 members including 1-3 hetero atoms, which are O, S, or N or combinations thereof, azido, amino, substituted amino, carbamoyloxy, alkoxy, alkylthio, carbamoylthio, thiocarbamoyloxy, N-($C_{1-6}$alkyl)carbamoyloxy, N-($C_{1-6}$alkyl)-thiocarbamoyloxy, N,N-di($C_{1-4}$alkyl)carbamoyloxy, N,N-di-($C_{1-6}$alkyl)thiocarbamoyloxy, quaternary ammonium, N,N-di($C_{1-6}$alkyl)-thiocarbamoyloxy, alkanoylcarbamoyloxy, hydroxyphenyl, sulfamoyloxy, alkylsulfonyloxy, or (cis-1,2-epoxypropyl)phosphone; and $R_B$ is $C_{1-6}$alkyl, $C_{2-6}$-alkanoyl, $C_{1-6}$alkoxy, $C_{1-6}$haloalkoxy, $C_{1-6}$alkylthio, $C_{1-6}$haloalkylthio, halo, $C_{1-6}$loweralkyl, $C_{2-6}$alkanoyloxy, $C_{1-6}$α-hydroxyalkyl, (β-substituted)ethyl, allyl, benzyl, nitroso, carbamoyl, ($C_{1-6}$alkoxy)carbonyl, sulfo, sulfamoyl, $C_{1-6}$alkylsulfo, phospho, nitro, carboxy, dithiocarboxy, carbobenzoxy, or dimethylaminomethyl.

We have now found a class of 7-substituted acylamino cephalosporins which have a high level of antibacterial activity against gram-negative organisms.

According to the present invention there is provided a compound of formula (I) or a pharmaceutically acceptable salt or in vivo hydrolysable ester thereof:

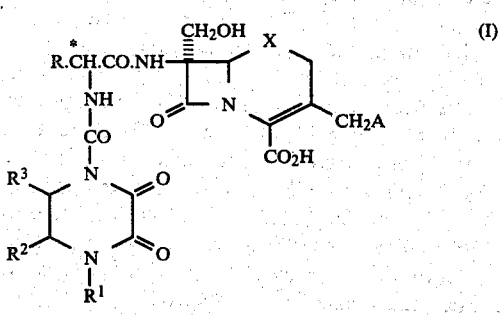

wherein
R is phenyl, 4-hydroxyphenyl, or a 5- or 6-membered heterocyclic ring containing up to three heteroatoms selected from oxygen, sulphur or nitrogen, optionally substituted with hydroxy, amino, halogen or $C_{1-6}$alkoxy;

$R^1$ represents hydrogen or $C_{1-6}$alkyl;

$R_2$ and $R^3$ are the same or different and represent hydrogen, $C_{1-6}$alkyl, halogen, amino, hydroxy, or $C_{1-6}$ alkoxy;

X represents oxygen or sulphur; and

A represents hydrogen, pyridyl, acetoxy, carbamoyloxy or a heterocyclicthio group.

The compounds of the present invention include the pharmaceutically acceptable esters of compound (I) which hydrolyse readily in the human body to produce the parent acid, for example acyloxyalkyl groups such as acetoxymethyl, pivaloyloxymethyl, α-acetoxyethyl and α-pivaloyloxyethyl groups; alkoxycarbonyloxyalkyl groups, such as ethoxycarbonyloxymethyl and α-ethoxycarbonyloxyethyl; dialkylaminoalkyl groups such as dimethylaminomethyl, dimethylaminoethyl, or diethylaminoethyl; and lactone groups such as phthalidyl or dimethoxyphthalidyl.

The compounds of the present invention also include the pharmaceutically acceptable esters of compound (I) which hydrolyse readily in the human body to produce the hydroxyl group of the 7-substituent, for example the formyl ester.

Suitable salts of the compounds of formula (I) include metal salts e.g. aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)amine or tri-(2-hydroxyethyl)amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabiethylamine, ethylenediamine, or bases of the pyridine type such as pyridine, collidine or quinoline, or other amines which have been used to form salts with known penicillins and cephalosporins.

The carbon atom marked * in formula (I) is asymmetric so that the compounds may exist as two optically active diastereoisomers. In general that prepared from the D-side chain exhibits the highest antibacterial activity.

In formula (I) the atom X is preferably sulphur.

In formula (I), the group R is preferably phenyl or 4-hydroxyphenyl, 2-thienyl, 3-thienyl or 2-amino-4-thiazolyl.

Suitable $C_{1-6}$ alkyl groups for the groups $R^1$, $R^2$ and $R^3$ include methyl, ethyl, n- and iso-propyl, n-, sec-, iso- and tert-butyl.

Preferably $R^1$ is ethyl.

Preferably $R^2$ and $R^3$ are hydrogen.

The group A may advantageously be a group of formula:

—S—Het wherein "Het" is a five or six-membered heterocyclic ring containing from 1 to 4 atoms selected from N, O, and S unsubstituted or substituted with one or two groups selected from $C_{1-6}$alkyl, $C_1$-$C_6$alkoxy, hydroxyalkyl, $C_1$-$C_6$alkenylalkoxyalkyl, carboxylalkyl, sulphonylalkyl, carbamoyl, carbamoylmethyl, trifluoromethyl, hydroxy, and halogen.

Examples of the group "Het" include unsubstituted and substituted diazolyl, triazolyl, tetrazolyl, thiazolyl, thiadiazolyl, thiatriazolyl, oxazolyl, and oxadiazolyl groups.

Suitable groups "Het" include unsubstituted and substituted 1,2,3-triazolyl; 1,2,4-triazolyl; 1,2,3,4-tetrazolyl; oxazolyl; thiazolyl; 1,3,4-oxadiazolyl; 1,3,4-thiadiazolyl, or 1,2,4-thiadiazolyl. Preferably, A is 1-methyl-(1H)-tetrazolylthio, 2-methyl-1,3,4-oxadiazol-5-ylthio, 1-carboxymethyl-(1H)-tetrazolylthio, pyridyl, or acetoxy.

Particular compounds within the scope of this invention include:

Sodium 7β-[2(4-ethyl-2,3-dioxopiperazine-1-carbonylamino)]phenylacetamido-7α-hydroxymethylcephalosporanate; Sodium 7β-[2(4-ethyl-2,3-dioxopiperazine-1-carbonylamino)]-phenylacetamido-7α-formyloxymethylcephalosporanate; Sodium 7β-[2-(4-ethyl-2,3-dioxopiperazine-1-carbonylamino)-2-(4-hydroxyphenyl)acetamido]-7α-hydroxymethylcephalosporanate; 7β-[2(4-ethyl-2,4-dioxopiperazine-1-carbonylamino)-2-phenylacetamido]-7α-hydroxymethyl-3-(1-methyl-1H-tetrazol-5-ylthio)methylceph-3-em-4-carboxylic acid.

The compounds of formula (I) may be prepared by reacting a compound of formula (II):

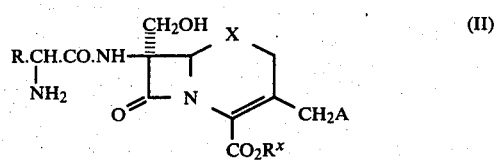

wherein the amino group is optionally substituted with a group which permits acylation to take place, X, R and A are defined with respect to formula (I) and any reactive substituents may be protected, and $R^x$ is hydrogen or a carboxyl-blocking group, with an N-acylating derivative of an acid of formula (III):

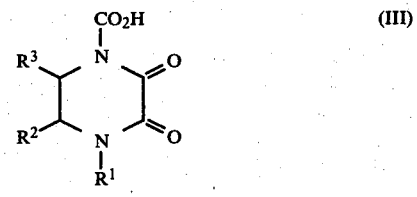

wherein $R^1$, $R^2$ and $R^3$ are as defined with respect to formula (I) above and any reactive groups may be protected; and thereafter, if necessary, carrying out one or more of the following steps:

(i) removing any carboxyl-blocking group $R^x$
(ii) removing any protecting groups on the side chain group;
(iii) converting the product into a salt or in vivo hydrolysable ester thereof.

Suitable groups which permit acylation to take place and which are optionally present on the amino group of the starting material of the formula (III) include N-silyl, N-stannyl and N-phosphorus groups, for example trialkylsilyl groups such as trimethylsilyl, trialkyltin groups such as tri-n-butyltin, groups of formula —P.$R^aR^b$ wherein $R^a$ is an alkyl, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being —P(OC$_2$H$_5$)$_2$, —P(C$_2$H$_5$)$_2$,

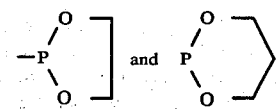

Suitable carboxyl-blocking derivatives for the group —CO$_2$R$^x$ in formula (II) include salts and ester derivatives of the carboxylic acid. The derivative is preferably one which may readily be cleaved at a later stage of the reaction. Suitable salts include metal salts, such as those with sodium, potassium and lithium, and tertiary amine salts, such as those with trilower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, such as described above, an oxime radical of formula —N=CHR$^o$ where R$^o$ is aryl or heterocyclic, or an in vivo hydrolysable ester radical such as defined above.

The carboxyl group may be regenerated from any of the above esters by usual methods appropriate to the particular R$^x$ group, for example, acid— and base—catalysed hydrolysis, or by enzymically-catalysed hydrolysis, or by hydrogenation.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be affected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a (C$_{1-6}$)-1,2,alkylene oxide—such as ethylene oxide or propylene oxide. The acylation reaction using an acid halide may be carried out at a temperature in the range −50° C. to +50° C., preferably −20° to +20° C., in aqueous or non-aqueous media such as aqueous acetone, aqueous tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting a compound of formula IV:

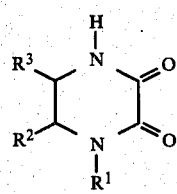
(IV)

wherein $R^1$, $R^2$ and $R^3$ are as defined with respect to formula (I) with a silylating agent and thereafter treating the N-silyl derivative with phosgene or carbonyl dibromide.

Suitable silylating agents include halosilanes or silazanes of the formulae.

$L_3$ Si U; $L_2$ Si $U_2$; $L_3$ Si $NL_2$;
$L_3$ Si NH Si $L_3$; $L_3$ Si.NH.COL; $L_3$ Si.NH.CO.NH.Si $L_3$;
L NH.CO.NH.Si $L_3$;

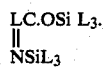

wherein U is a halogen and the various groups L which may be the same or different, each represents hydrogen or alkyl, alkoxy, aryl, or aralkyl. Preferred silylating agents are silyl chlorides, particularly trimethylchlorosilane, and dimethyldichlorosilane.

The intermediate compound of formula (II) may be prepared by reacting a compound of formula (V):

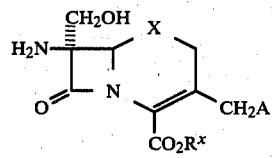
(V)

wherein the amino group is optionally substituted with a group which permits acylation to take place and $R^x$ and X as defined with respect to formula (II) above, with an N-acylating derivative of an acid of formula (VI)

(VI)

wherein R is as defined with respect to formula (I) and any reactive groups therein may be protected and $R^y$ is an amino-protecting group; and thereafter removing protecting group $R^y$.

Suitable N-acylating derivatives, carboxyl protecting groups and reaction conditions include those described hereinbefore.

Suitable amino-protecting groups $R^y$ are those well-known in the art which may be removed under conventional conditions without disruption of the remainder of the molecule.

The starting material of formula (V) is disclosed in British Pat. No. 1366682.

The compounds of formula (I) may also be prepared by reacting a compound of formula (V) as described hereinbefore with an N-acylating derivative of an acid of formula (VI):

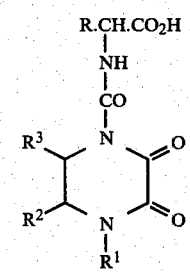
(VI)

where R, $R^1$, $R^2$ and $R^3$ are as defined with respect to formula (I) and any reactive groups therein may be protected; and thereafter, if necessary, carrying out one or more of the following steps:
(i) removing any carboxyl-blocking group $R^x$
(ii) removing any protecting groups on the side chain group;
(ii) converting the product into a salt or in vivo hydrolysable ester thereof.

Compounds of formula (I) wherein A represents a heterocyclic thio group may also be prepared by reaction of a compound of formula (VII):

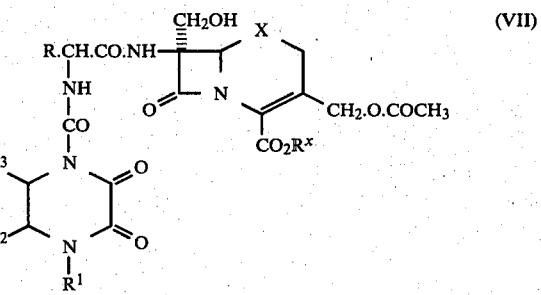
(VII)

wherein R, $R^1$, $R^2$, $R^3$ and X are as defined with respect to formula (I) above and $R^x$ is hydrogen or a carboxyl blocking group as defined with respect to formula (II) above and wherein any reactive groups may be protected; with a thiol of formula:

HetSH wherein Het is as defined hereinbefore, and thereafter where necessary carrying out one or more of the following steps:
(a) removing any carboxyl-blocking groups $R^x$,
(ii) removing any protecting groups on the substituent groups,
(iii) converting the product into a salt or in vivo hydrolysable ester thereof.

The thiol HetSH may be reacted as the free compound or a salt with an alkali metal such as sodium or potassium. This reaction is desirably conducted in a solvent. For example, use can be made of water, or organic solvents readily miscible with water and inert to the staring compounds, such as dimethylformamide, dimethylacetamide, dioxane, acetone, alcohol, acetonitrile, dimethylsulfoxide or tetrahydrofuran. The reaction temperature and time depend, among other factors, upon the starting compounds and solvent to be employed but generally the reaction is carried out at a selected temperature within the range of 0° to 100° C. for a selected time of a few hours to several days. The reaction is desirably conducted in the neighbourhood of neutrality or between pH 2 and 8 and, for better results, between pH 5 and 8. To prevent oxidation of the thio compounds it is advantageous to carry out the reaction in an inert gaseous atmosphere, e.g. nitrogen gas.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route, such as oral topical or parenteral. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anaesthetic, preservative and buffering agents can be dissolved in the vehicle. To enhance the stability, the compositon can be frozen after filling into the vial and the water removed under vaccuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration.

The compound of formula (I) may be the sole therapeutic agent in the compositions of the invention, or a combination with other antibiotics or with a β-lactamase inhibitor may be employed.

Advantageously the compositions also comprise a compound of formula (VIII) or a pharmaceutically acceptable salt or ester thereof:

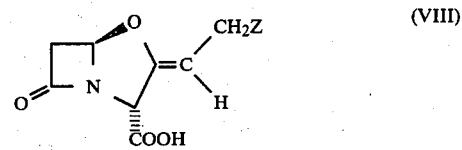

(VIII)

wherein Z is hydroxyl, substituted hydroxyl, thiol, substituted thiol, amino, mono- or di-hydrocarbyl-substituted amino, or mono- or di-acylamino.

The following Examples illustrate the preparation of some of the compounds of this invention.

EXAMPLE 1

(a) tert-Butyl N-p-nitrobenzylidene-7α-hydroxymethyl-7β aminocephalosporanate

Anhydrous potassium carbonate (1.496 g, 0.0108 mol) was added to a cooled (CCl$_4$-solid CO$_2$) solution of tert-butyl N-p-nitrobenzylidene-7β-aminocephalosporanate (5.0 g, 0.0108 mol) in dry N,N-dimethylformamide (250 cm$^3$) and the mixture stirred for 5 min. A stream of gaseous formaldehyde, prepared by heating dry paraformaldehyde at 175° C. under a stream of dry nitrogen, was then passed over the above-mentioned solution for 30 min. The flow of gas was stopped and, after stirring for 5 min, the reaction mixture was diluted with ether (500 cm$^3$) and stirred for a further 10 min, and the cooling bath removed. The solution was partitioned with dilute brine and the emulsified aqueous layer separated, and passed through a bed of celite. This aqueous layer was reextracted with ether (100 cm$^3$) and the mixed organic fractions extracted with dilute brine (6 x). The organic solution was dried (MgSO$_4$) and evaporated to give the title compound (3.85 g, 72%) as a pale orange solid. $\nu_{max}$ (KBr) 3530, 3440, 1770, 1750, 1720, 1640, 1605, 1525, 1390, 1370 and 1350 cm$^{-1}$, δ(CDCl$_3$) 1.57 (9H, s, CMe$_3$), 2.10 (3H, s, OCOMe), 3.07 br (1H, s, CH$_2$OH), 3.50 (2H, ABq, J 18 Hz, S.CH$_2$·C), 4.20 br (2H, s, CH$_2$OH), 4.98 (2H, ABq, J 14 Hz, C.CH$_2$.OCO), 5.26 (1H, s, C.CH.S), 8.24 (2H, ABq, J 9 Hz, aromatic H), and 8.98 (1H, s, CH:N) (addition of D$_2$O caused the signal at 3.07 to disappear).

(b) tert-Butyl 7α-hydroxymethyl-7β-aminocephalosporanate tert-Butyl N-p-nitrobenzylidene-7α-hydroxymethyl-7β-aminocephalosporanate (0.491 g, 1 mmol) in the minimum quantity of ethyl acetate was added to a mixture of pulvarized 2,4-dinitrophenylhydrazine (0.285 g, 1.44 mmol) and p-toluenesulphonic acid monohydrate (0.274 g, 1.44 mmol) in ethanol (10 cm$^3$), which had been previously stirred for 1 h. After stirring for a further 1 hr, the mixture was centrifuged and the liquor decanted. This solution was evaporated to a yellow gum, redissolved in ethyl acetate and extracted sequentially with dilute sodium hydrogen carbonate solution, saturated brine, followed by dilute hydrochloric acid (3 x). The combined acid extracts were washed once with ethyl acetate and the organic layer was discarded. The aqueous layer was neutralised by the careful addition of solid sodium carbonate and then extracted with ethyl acetate (3 x). The combined organic extracts were dried (MgSO$_4$), and evaporated to afford the product (0.272 g, 76%) as a yellow syrup. $\delta$(CDCl$_3$) 1.56 (9H, s, CMe$_3$), 2.13 (3H, s, OCOMe), 2.88 br (3H, s, NH$_2$ and OH), 3.63 (2H, AB q, J 18 Hz, S.CH$_2$.C), 4.01 (2H, s, C.CH$_2$.OH), 4.93 (1H, s, C.CH.S), and 4.98 (2H, AB q, J 13 Hz, C.CH$_2$.OCO) (addition of D$_2$O caused the signal at 2.88 to disappear).

(c) tert-Butyl 7$\beta$-[D,2(4-ethyl-2,3-dioxopiperazine-1-carbonylamino)]phenylacetamido-7$\alpha$-hydroxymethylcephalosporanate Freshly prepared D,2(4-ethyl-2,3-dioxopiperazine-1-carbonylamino) phenylacetyl chloride, generated by the treatment of the corresponding acid (0.449 g, 1.34 mmol) with oxalyl chloride (0.170 g, 1.34 mmol) and N,N-dimethylformamide (1 drop) at 0° C. in dichloromethane (10 cm$^3$) was added to a solution of tert-butyl 7$\alpha$-hydroxymethyl-7$\beta$-aminocephalosporanate (0.300 g, 0.838 mmol) in dichloromethane (5 cm$^3$) at 0° C., followed by pyridine (0.066 g, 0.838 mmol). After stirring for a further 30 min, the reaction mixture was diluted with dichloromethane and washed sequentially with dilute hydrochloric acid, saturated sodium hydrogen carbonate solution, and saturated brine. The organic layer was dried (MgSO$_4$) and evaporated to afford a yellow syrup which, after silica-gel column chromatography [EtOAc-petroluem ether (b.p. 60°–80° C.) as eluant], gave the title compound (0.095 g, 17%) as a clear gum. $\nu_{max}$ (film) 3400, 3300, 1780, 1720 br, 1690, and 1520 cm$^{-1}$ $\delta$(CDCl$_3$) 1.18 (3H, t, J 7 Hz, N.CH$_2$.CH$_3$), 1.48 (9H, s, CMe$_3$), 2.02 (3H, s, OCOMe), 3.08 and 3.35 (2H, AB q, J 19 Hz, S.CH$_2$.C), 3.40–3.70 (4H, m, CH$_2$.N.CH$_2$), 3.99 (2H, m, N.CH$_2$.CH$_2$), 4.20 (1H, s, CH$_2$.OH), 4.11 and 4.29 (2H, AB q, J 12 Hz, C.CH$_2$.OH), 4.70 and 5.01 (2H, AB q, J 14 Hz, C.CH$_2$.OCO), 4.90 (1H, s, C.CH.S) 5.61 (1H, d, J 6 Hz, Ph.CH.NH), 7.2–7.6 (5H, m, Ph), 7.70 (1H, s, CO.NH.C), and 9.92 (1H, d, J 6 Hz, CH.NH.CO) (irradiation at 3.45 caused the signal at 1.18 to collapse to a s and irradiation at 9.92 caused the signal at 5.61 to collapse to a s; addition of D$_2$O caused the signals at 7.70 and 4.20 to disappear).

Another material was separated by chromatography and characterised as described in Example 2.

(d) Sodium 7$\beta$-[2(4-ethyl-2,3-dioxpiperazine-1-carbonylamino)]phenylacetamido-7$\alpha$-hydroxymethylcephalosporanate tert-Butyl 7$\beta$-[2(4-ethyl-2,3-dioxopiperazine-1-carbonylamino)]phenylacetamido-7$\alpha$-hydroxymethylcephalosporanate (0.060 g, 0.091 mmol) was taken up in trifluoroacetic acid (0.5 cm$^3$) and the mixture allowed to stand at ambient temperature for 1 h. The solvent was then evaporated in vacuo; the complete removal of trifluoroacetic acid being ensured by the addition of toluene (2 × 1 cm$^3$) and its evaporation. The residue was taken up in acetone (0.5 cm$^3$) and 2 M-sodium ethyl hexanoate (0.045 cm$^3$) in methyl isobutyl ketone added, followed by dry ether (ca. 1 cm$^3$). The precipitated solid was filtered, washed well with dry ether and dessicated to furnish the title compound (0.050 g, 88%) as an amorphous pale white solid. $\delta$[(CD$_3$)$_2$SO] 1.07 (3H, t, J 7 Hz, N.CH$_2$CH$_3$), 1.97 (3H, s, OCOMe), 3.0–4.3 (10H, m, S.CH$_2$.C.C.CH$_2$OH, N.CH$_2$.CH$_3$, and N.CH$_2$.CH$_2$.N), 4.76 (2H, AB q, J 14 Hz, C.CH$_2$.OCO), 4.93 (1H, s, C.CH.S), 5.64 (1H, d, J 7 Hz, Ph.CH.NH), 7.2–7.6 (5H, m, Ph), 9.08 (1H, s, CO.NH.C), and 9.80 (1H, d, J 7 Hz, Ph.NH.CH) (addition of D$_2$O caused the signals at 9.08 and 9.80 to disappear and that at 5.64 to collapse to a s).

EXAMPLE 2

(a) tert-Butyl 7$\beta$-[2(4-ethyl-2,3-dioxopiperazine-1-carbonylamino)]phenylacetamido-7$\alpha$-formyloxymethylcephalosporanate The second product isolated after column chromatography in Example 1(c) was the title compound (0.048 g, 5%) as a colourless gum: $\nu_{max}$ (soln) 3400, 3300, 1780, 1740, 1720, 1690 and 1640 cm$^{-1}$. $\delta$(CDCl$_3$, 250 MHz) 1.22 (3H, t, J 7 Hz, N.CH$_2$.CH$_3$), 1.51 (9H, s, CMe$_3$), 2.08 (3H, s, OCOMe), 3.17 and 3.44 (2H, each d, J 19 Hz, S.CH$_2$.C), 3.42–3.66 (4H, m, CH$_2$.N.CH$_2$.CH$_3$), 3.92–4.22 (2H, m, N.CH$_2$.CH$_2$), 4.75 and 5.04 (2H, each d, J 14 Hz, C.CH$_2$.OCOMe), 4.78 and 4.92 (2H, each d, J 13 Hz, C.CH$_2$OCOH), 4.95 (1H, s, C.CH.S), 5.54 (1H, d, J 6.5 Hz, Ph.CH.NH), 6.86 (1H, s., CO.NH.C), 7.32–7.50 (5H, m, Ph), 8.05 (1H, s, CH$_2$OCOH), and 9.97 (1H, d, J 6.5 Hz, CH.NH.CO) (irradiation at 3.50 caused the signal at 1.22 to collapse to a s whilst irradiation at 9.97 caused the signal at 5.54 to collapse to a s; addition of D$_2$O caused the signal at 6.86 to disappear). In the $^{13}$C-n.m.r. spectrum the CH$_2$OCOH moiety resonated at the following: $\delta$(CDCl$_3$) proton-decoupled mode; multiplicity deduced from an off-resonance-decoupled spectrum) 61.195 (t, CH$_2$) and 159.764 (d, OCOH).

(b) Sodium 7$\beta$-[2(4-ethyl-2,3-dioxopiperazine-1-carbonylamino)]phenylacetamido-7$\alpha$-formyloxymethylcephalosporanate The cephalosporin ester from Example 2(a) (0.08 g, 0.114 mmol) was treated with TFA (1 ml) for 45 min., after which time the excess acid was evaporated to give 7$\beta$-[2(4-ethyl-2,3-dioxopiperazine-1-carbonylamino)]phenylacetamido-7$\alpha$-formyloxymethylcephalosporanic acid as a light yellow solid, $\delta$[(CD$_3$)$_2$CO] 1.20 (3H, t, J 7 Hz, N.CH$_2$CH$_3$), 2.00 (OCOMe, obscured by acetone), 3.3–4.4 (8H, m, N.CH$_2$.CH$_2$.N.CH$_2$.CH$_3$ and S.CH$_2$.CO), 4.7–5.4 [5H, m, C.CH$_2$.OCOH, C.CH$_2$OCOMe and C.CH.S (s at 5.12 discernable)], 5.70 (1H, d, J 6.5 Hz, NH.CH.CO), 7.3–7.8 (5H, m, Ph), 8.15 (1H, s, CH$_2$OCOH), 8.50 br and 8.70 br (each 1H, s, CO$_2$H and C.NH.C), and 9.90 (1H, d, J 6.5 Hz, CO.NH.CH).

An acetone solution of the above-mentioned acid was treated with 2 M-SEH (0.057 ml) and a solid precipitated with the aid of dry Et$_2$O. The resulting solid was washed well with acetone: Et$_2$O mixture to afford the title compound (0.063 g, 83%) as an amorphous white solid; δ[(CD₃)₂SO] 1.08 (3H, t, J 7 Hz, N.CH₂.C$\underline{H}$₃), 1.96 (3H, s, OCOMe), 3.1–3.7 [7H, m, C$\underline{H}$₂.N.C$\underline{H}$₂.CH₃, C.CH₂.O$\underline{H}$, S.CH₂.C, obscured by HOD], 3.8–4.1 (2H, m, N.C$\underline{H}$₂.CH₂.N), 4.55–5.0 [5H, m, C.C$\underline{H}$₂.OCOH, C.C$\underline{H}$₂OCOMe and C.CH.S (s at 4.94 discernable)], 5.65 (1H, d, J 7 Hz, NH.C$\underline{H}$.CO), 7.2–7.6 (5H, m, Ph), 8.27 (1H, s, CH₂OCO$\underline{H}$), 9.33 (1H, s, CO.NH.C), and 9.77 (1H, d, J 7 Hz, CO.N$\underline{H}$.CH) (addition of D₂O caused the signals at 9.33 and 9.77 to disappear and that at 5.65 to collapse to a s).

EXAMPLE 3

Sodium
7β-[2-(4-ethyl-2,3-dioxopiperazine-1-carbonylamino)-2-(4-hydroxyphenyl)acetamido]-7α-hydroxymethylcephalosporanate (a) tert-Butyl
7β-[2-(4-ethyl-2,3-dioxopiperazine-1-carbonylamino)-2-(4-benzyloxycarbonyloxy)phenyl]acetamido-7α-hydroxymethylcephalosporanate Freshly prepared D-[2-(4-ethyl-2,3-dioxopiperazine-1-carbonylamino)-2-(4-benzyloxycarbonyloxy)phenyl]acetyl chloride, generated by the treatment of the corresponding acid (0.653 g, 1.4 mmol) with oxalyl chloride (0.121 ml, 1.4 mmol) and N,N-dimethylformamide (2 drops) at 0° C. in dichloromethane (20 ml) for two hours was added to a solution of tert-butyl 7α-hydroxymethyl-7β-aminocephalosporanate (0.5 g, 1.4 mmol) in dichloromethane (10 ml) at 0° C., followed by pyridine (0.113 ml, 1.4 mmol). After stirring for 30 min., the reaction mixture was allowed to approach room temperature. After 60 min., aqueous work-up as described in Example 1(c), followed by silica gel chromatography [EtOAc-petroleum ether (b.p. 60°–80° C.) as eluant] gave the product (0.176 g, 16%) as a clear gum. ν$_{max}$ (film) 3450, 3300, 1780, 1765, 1720 and 1695 cm⁻¹, δ(CDCl₃) 1.18 (3H, t, J 7 Hz, N.CH₂.C$\underline{H}$₃), 1.50 (9H, s, CMe₃) 2.03 (3H, s, OCOMe), 2.20 br (1H, OH), 3.20 (2H, ABq, J 18 Hz, S.CH₂.C), 3.3–3.7 (4H, m, C$\underline{H}$₂.N.C$\underline{H}$₂.CH₃), 3.8–4.1 (2H, m, N.C$\underline{H}$₂.CH₂), 4.1–4.4 (2H, m, C.C$\underline{H}$₂OH), 4.85 (2H, ABq, J 14 Hz, C.CH₂.OCO), 4.88 (1H, s, C.CH.S), 5.23 (2H, s, O.C$\underline{H}$₂.Ph), 5.64 (1H, d, J 6.5 Hz, NH.C$\underline{H}$.CO), 7.11 and 7.55 (4H, each d, J 9 Hz, aromatic H), 7.38 (5H, s, Ph), 7.9 (1H, s, CO.NH.C), and 9.98 (1H, d, J 6.5 Hz, CH.N$\underline{H}$.CO) [addition of D₂O caused the signals at 2.20, 7.90 and 9.98 to disappear whilst that at 5.64 collapsed to a s and the m at 4.1–4.4 collapsed to an ABq (J 12 Hz centred at 4.20].

(b) Sodium
7β-[2-(4-ethyl-2,3-dioxopiperazine-1-carbonylamino)-2-(4-hydroxyphenyl)acetamido]-7α-hydroxymethylcephalosporanate The tert-butyl ester from Example 3(a) (0.065 g, 0.08 mmol) in THF:H₂O (4+2 ml) was hydrogenolysed over 10% palladium—charcoal (0.07 g) for 1.75 h. The mixture was then filtered through celite and the celite washed well with THF (10 ml), followed by ethyl acetate (10 ml). This mixture was concentrated in vacuo until a milky solution remained, which was extracted well with ethyl acetate (2 x) and the combined organic extracts dried (MgSO₄) and evaporated to give tert-butyl
7β-[2-(4-ethyl-2,3-dioxopiperazine-1-carbonylamino)-2-(4--hydroxyphenyl)acetamido]-7α-hydroxymethylcephalosporanate (0.045 g, 81%) as a colourless syrup.

The above ester (0.045 g, 0.068 mmol) was taken up in TFA (1 ml) and after 1 h at room temperature, subjected to evaporation in vacuo; the complete removal of TFA being ensured by the addition of toluene (2 × 1 ml) and its evaporation. The residue was taken up in acetone (1 ml) and 2M-SEH (0.034 ml) added, followed by ether. The precipitated solid was centrifuged and washed well with acetone:ether (1:1; 2 ml) and dessicated to furnish the title compound (0.028 g, 66%) as an amorphous solid, δ(D₂O, 250 MHz) 1.15 (3H, t, J 7 Hz, N.CH₂.C$\underline{H}$₃), 2.04 (3H, s, OCOMe), 3.14 and 3.49 (2H, each d, J 18 Hz, S.CH₂C), 3.46 (2H, q, J 7 Hz, N.C$\underline{H}$₂.CH₃) 3.57–3.72 (2H, m, C$\underline{H}$₂.N.CH₂), 3.84–4.02 (2H, m, CO.N.CH₂), 4.09 (2H, ABq, J 12.5 Hz, C.C$\underline{H}$₂OD), 4.60 and 4.85 (2H, each d, J 13 Hz, C.C$\underline{H}$₂OCO), 4.99 (1H, s, C.CH.S), 5.14 (1H, s, ND.CH.CO), and 6.88 and 7.34 (4H, each d, J 9 Hz, aromatic H).

EXAMPLE 4

7β-[2(4-Ethyl-2,3-dioxopiperazine-1-carbonylamino)-2-phenylacetamido]-7α-hydroxymethyl-3-(1-methyl-1H-tetrazol-5-ylthio)methylceph-3-em-4-carboxylic acid tert-Butyl 7β-[D,2(4-ethyl-2,3-dioxopiperazine-1-carbonylamino)]phenylacetamido-7α-hydroxymethylcephalosporanate (0.184, 0.273 mmol) was dissolved in trifluoroacetic acid (5 ml) and the solution allowed to stand at room temperature for 1 hr. The solvent was then evaporated in vacuo; the removal of excess acid being ensured by the addition of toluene (2×2 ml) and its evaporation. The yellow residue was taken up in phosphate buffer (pH 6.5; 10 ml) and 1-(H)-1-methyl-5-mercaptotetrazole (0.038 g, 0.327 mmol) added and the pH adjusted to 6.5 (dil. aq. NaHCO₃). This mixture was stirred at 60° C. for 6 hours whilst maintaining the pH at 6.5. The reaction mixture was then cooled, covered with ethyl acetate and the pH lowered to 2 (1 N-HCl). The organic fraction was separated and the aqueous fraction extracted (2 x) with ethyl acetate, the organic extracts combined, dried (MgSO₄), and evaporated to give a yellow solid which was taken up in water at neutral pH. This solution was extracted with ethyl acetate and the pH of the separated aqueous layer lowered to 4, followed by extraction with ethyl acetate (4 x). The resulting aqueous fraction was covered with n-butanol, the pH lowered to 1.5 and organic phase separated. The aqueous layer was partitioned once more with n-butanol and the butanol extracts combined and evaporated to give a white solid which was triturated well with dry ether. The residual white solid (0.031 g, 17%) was the title compound: (δCDCl₃, 250 MHz) 1.18 (3H, t, J 7 Hz, N.CH₂.C$\underline{H}$₃), 3.45–3.60 (5H, m, S.CH₂.C, NC$\underline{H}$₂.CH₃ and CH₂.O$\underline{H}$) 3.68–3.80 (2H, m, CO.N.CH₂) 3.98 (3H, s, N-Me), 3.95–4.12 (2H, m, N.C$\underline{H}$₂.CH₂), 4.18 (2H, ABq, J 13 Hz, C.C$\underline{H}$₂.OH), 4.34 (2H, ABq, J 14 Hz, C.CH₂.S.Tet), 5.07 (1H, s, C.CH.S), 5.65 (1H, d, J 7 Hz, NH.C$\underline{H}$.CO), 7.3–7.6 (5H, m, Ph), 8.26 (1H, s, CO.NH.C), and 9.98 (1H, d, J 7 Hz, CH.N$\underline{H}$.CO) (addition of D₂O caused the signal at 8.26 to disappear; irradiation at 9.98 caused the signal at 5.65 to collapse to a d whilst irradiation at 1.18 caused the signals in the 3.45–3.60 to modify).

EXAMPLE 5

Diphenylmethyl 7β-amino-7α-hydroxymethyl-3-(1-methyl-1H-tetrazol-5-ylthio)methylceph-3-em-4-carboxylate tert-Butyl 7β-amino-7α-hydroxymethylcephalosporanate (0.775 g, 2.17 mmol) was dissolved in trifluoroacetic acid (10 ml) and after standing at ambient temperature for 1 hour, the solvent evaporated. The resulting yellow syrup was taken up in phosphate buffer (pH 6.5, 50 ml) and 1-(H)-1-methyl-5-mercaptotetrazole (0.250 g, 2.16 mmol) added. The pH of the solution was adjusted to 6.5 and the mixture stirred at 60° C. whilst maintaining the pH at 6.5. After 6 hours, the reaction mixture was cooled, filtered, covered with ethyl acetate and the pH lowered to 4. The separated aqueous extract was partitioned with ethyl acetate and the organic fractions discarded. The aqueous fraction was evaporated in vacuo to give a brown syrup which contained traces of water. This syrup was taken up in dioxan (10 ml), a dichloromethane solution of diphenyldiazomethane added and this solution stirred vigorously for 48 hours. The resulting mixture was neutralised by the addition of 50% acetic acid (10 ml) and the ethyl acetate (50 ml) added. The solution was washed with saturated aqueous sodium hydrogen carbonate, followed by brine. The dried ($MgSO_4$) organic fraction was evaporated to give a yellow syrup which, after silica gel column chromatography, gave the ester (0.150 g, 13%); it possessed the following characteristics. $\nu_{max}$ (film) 3400, 1780, 1730 and 1660 $cm^{-1}$, δ($CDCl_3$, 250 MHz) 2.0 br (2H, $NH_2$), 3.74 (2H, ABq, J 19 Hz, $CH.S.CH_2.C$), 3.8–3.9 br (1H, OH), 3.85 (3H, s, N.Me), 3.96 (2H, s, $CH_2.OH$), 4.33 (2H, ABq, J 16 Hz, $C.CH_2.S.C$), 4.85 (1H, s, C.CH.S), 6.93 (1H, s, $CH.Ph_2$), and 7.2–7.5 (10H, m, $CH.Ph_2$), m/e 438

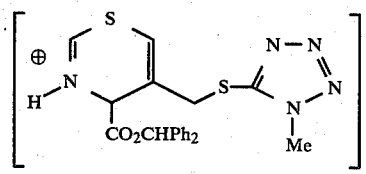

and 167 ($Ph_2C^{61}$ H, base peak).

DEMONSTRATION OF EFFECTIVENESS

| Organism | MIC (μg/ml) |
|---|---|
| MIC values (μg/ml) for compound of Example 1d | |
| E. coli ESS | <0.02 |
| E. coli JT 4 | 5.0 |
| E. coli JT 425 | 2.5 |
| E. coli NCTC 10418 | 2.5 |
| Ps aeruginosa NCTC 10662 | >100 |
| Ps aeruginosa NCTC 10662 $10^{-2}$ | >100 |
| Ps aeruginosa Dalgleish $10^{-2}$ | >100 |
| S. marcescens US 32 | 5.0 |
| K. aerogenes A | 0.5 |
| E. cloacae Nl | 10 |
| P. mirabilis C 977 | 2.5 |
| P. mirabilis 889 | 1.0 |
| P. morganii | 10 |
| P. rettgeri | 10 |
| B. subtilis | >100 |
| S. aureus Oxford | >100 |
| S. aureus Russell | >100 |
| N. catarrhalis 1502 | 0.2 |
| S. faecalis I | >100 |
| S. pyogenes CN 10 | 100 |

-continued
DEMONSTRATION OF EFFECTIVENESS

| Organism | MIC (μg/ml) |
|---|---|
| MIC values (μg/ml) for compound of Example 3b | |
| E. coli ESS | 0.05 |
| E. coli JT 4 | 2.5 |
| E. coli JT 425 | 1.0 |
| E. coli NCTC 10418 | 1.0 |
| Ps aeruginosa NCTC 10662 | 50 |
| Ps aeruginosa NCTC 10662 $10^{-2}$ | 50 |
| Ps aeruginosa Dalgleish $10^{-2}$ | 25 |
| S. marcescens US 32 | 5 |
| K. aerogenes A | 0.25 |
| E. cloacae Nl | 10 |
| P. mirabilis C 977 | 2.5 |
| P. mirabilis 889 | 0.5 |
| P. morganii | 10 |
| P. rettgeri | 10 |
| B. subtilis | >100 |
| S. aureus Oxford | >100 |
| S. aureus Russell | >100 |
| N. catarrhalis 1502 | 0.5 |
| S. faecalis I | >100 |
| S. pyogenes CN 10 | >100 |
| MIC values (μg/ml) for compound of Example 4 | |
| E. coli ESS | <0.02 |
| E. coli JT 4 | 5.0 |
| E. coli JT 425 | 1.0 |
| E. coli NCTC 10418 | 1.0 |
| Ps aeruginosa NCTC 10662 | >100 |
| Ps aeruginosa NCTC 10662 $10^{-2}$ | >100 |
| Ps aeruginosa Dalgleish $10^{-2}$ | 100 |
| S. marcescens US 32 | 5.0 |
| K. aerogenes A | 0.2 |
| E. cloacae Nl | 25 |
| P. mirabilis C 977 | 5.0 |
| P. mirabilis 889 | 2.5 |
| P. morganii | 10 |
| P. rettgeri | 25 |

We claim:

1. A compound of formula (I) or a pharmaceutically acceptable salt or in vivo hydrolysable ester thereof:

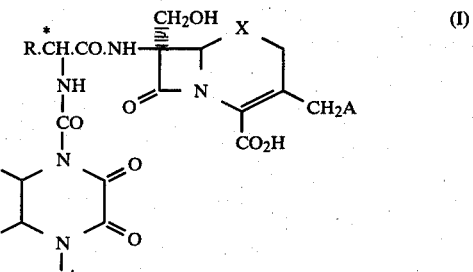

wherein

R is phenyl, 4-hydroxyphenyl, or a 5- or 6-membered heterocyclic ring containing up to three heteroatoms selected from oxygen, sulphur or nitrogen, optionally substituted with hydroxy, amino, halogen or $C_{1-6}$ alkoxy;

$R^1$ represents hydrogen or $C_{1-6}$ alkyl;

$R^2$ and $R^3$ are the same or different and represent hydrogen, $C_{1-6}$ alkyl, halogen, amino, hydroxy, or $C_{1-6}$ alkoxy;

X represents oxygen or sulphur; and

A represents hydrogen, or acetoxy.

2. A compound as claimed in claim 1 wherein the carbon atom marked * in formula (I) is in the D configuration.

3. A compound as claimed in claim 1 wherein X is sulphur.

4. A compound as claimed in claim 1 wherein R is phenyl or 4-hydroxyphenyl, 2-thienyl, 3-thienyl or 2-amino-4-thiazolyl.

5. A compound as claimed in claim 1 wherein $R^1$, $R^2$ and $R^3$ may be the same or different and each represents methyl, ethyl, n- and iso- propyl, n-, sec-, iso- and tert-butyl.

6. A compound as claimed in claim 1 wherein $R^1$ is ethyl.

7. A compound as claimed in claim 1 wherein $R^2$ and $R^3$ are hydrogen.

8. A compound as claimed in claim 1 or a pharmaceuticaly acceptable salt or in vivo hydrolysable ester thereof which is:

7β-[2(4-ethyl-2,3-dioxopiperazine-1-carbonylamino)]phenylacetamido-7α-hydroxymethylcephalosporanic acid; 7β-[2(4-ethyl-2,3-dioxopiperazine-1-carbonylamino)]phenylacetamido-7α-formyloxymethylcephalosporanic acid; 7β-[2-(4-ethyl-2,3-dioxopiperazine-1-carbonylamino)-2-(4-hydroxyphenyl)acetamido]-7α-hydroxymethylcephalosporanic acid.

9. A pharmaceutical composition having antibacterial activity comprising an antibacterially effective amount of a compound as claimed in claim 1 together with a pharmaceutical carrier or excipient.

10. A pharmaceutical composition according to claim 9 which also comprises a compound of formula (VIII) or a pharmaceutically acceptable salt or ester thereof:

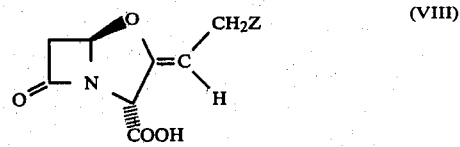

wherein Z is hydroxyl, substituted hydroxyl, thiol, substituted thiol, amino, mono- or di-hydrocarbyl-substituted amino, or mono- or di-acylamino.

11. A method of treating an antibacterial infection in a host in need thereof which comprises the administration to such host of an effective amount of a composition of claim 9.

12. A method of treating an antibacterial infection in a host in need thereof which comprises the administration to such host of an effective amount of a composition of claim 10.

13. A compound according to claim 1, wherein R is 4-hydroxyphenyl, $R^1$ is ethyl, $R^2$ and $R^3$ are each hydrogen, X is oxygen and A is acetoxy.

* * * * *